United States Patent
Coumans et al.

(10) Patent No.: US 7,777,885 B2
(45) Date of Patent: Aug. 17, 2010

(54) DIAGNOSTIC IMAGING DEVICE FOR THE ANALYSIS OF CIRCULATING RARE CELLS

(75) Inventors: Frank A. W. Coumans, GD Stein, NE (US); Arthur G. Marlin, Willow Grove, PA (US); Frank P. Modica, Princeton, NJ (US); John V. Verrant, Solebury, PA (US)

(73) Assignee: Veridex, LLC, Raritan, NJ (US)

( * ) Notice: Subject to any disclaimer, the term of this patent is extended or adjusted under 35 U.S.C. 154(b) by 186 days.

(21) Appl. No.: 11/701,765

(22) Filed: Feb. 2, 2007

(65) Prior Publication Data

US 2007/0153280 A1  Jul. 5, 2007

(51) Int. Cl.
*G01N 21/25* (2006.01)

(52) U.S. Cl. .............................. 356/417; 435/2; 435/6; 435/7.23

(58) Field of Classification Search ................. 356/417; 435/2, 6, 7.23, 7.24, 69.3, 70.2, 172
See application file for complete search history.

(56) References Cited

U.S. PATENT DOCUMENTS

| | | | |
|---|---|---|---|
| 5,186,827 A | 2/1993 | Liberti | |
| 5,698,271 A | 12/1997 | Liberti | |
| 5,985,153 A | 11/1999 | Dolan | |
| 5,993,665 A | 11/1999 | Terstappen | |
| 6,120,856 A | 9/2000 | Liberti | |
| 6,365,362 B1 | 4/2002 | Terstappen | |
| 6,551,843 B1 | 4/2003 | Rao | |
| 6,620,627 B1 | 9/2003 | Liberti | |
| 6,645,731 B2 | 11/2003 | Terstappen | |
| 6,861,259 B2 | 3/2005 | Columbus | |
| 6,863,362 B2 * | 3/2005 | Reichel et al. | 347/19 |
| 7,011,794 B2 | 3/2006 | Kagan | |
| 2005/0063863 A1 | 3/2005 | Columbus | |
| 2005/0181463 A1 * | 8/2005 | Rao et al. | 435/7.23 |
| 2006/0115380 A1 | 6/2006 | Kagan | |
| 2008/0176332 A1 * | 7/2008 | Berns et al. | 436/55 |

\* cited by examiner

*Primary Examiner*—Gregory J Toatley, Jr.
*Assistant Examiner*—Iyabo S Alli (57) ABSTRACT

The present invention provides a system for imaging circulating tumor cells from blood after enrichment. The system is designed to provide optimum use in a clinical laboratory setting with minimum laboratory bench top space. Operator intervention is minimized compared to other analytical methodologies. The system is useful in the enumeration and identification of target cells in a sample specimen for screening and detection of early stage pre-metastatic cancer, monitoring for disease remission in response to therapy and selection of more effective dose regimens or alternative therapies for individual patients.

10 Claims, 11 Drawing Sheets

Figure 1

Panel-A

Panel-B

Panel A:

Panel B:

Panel C:

Panel A

Panel B

DIAGNOSTIC IMAGING DEVICE FOR THE ANALYSIS OF CIRCULATING RARE CELLS

PRIORITY INFORMATION

This application claims priority under 35 USC 119(e) to U.S. Provisional Application Nos. 60/602,504, filed 17 Aug. 2004; 60/645,683, filed 21 Jan. 2005; and 60/648,477, filed 31 Jan. 2005.

FIELD OF THE INVENTION

This invention relates generally to the field of automated sample imaging, and more particularly to image cytometry of isolated rare cells from body fluids by an automated device for analysis relating to the diagnosing, monitoring and managing of specific diseases, particularly cancer.

BACKGROUND ART

Tumor cells are often present in blood of carcinoma patients as rare cells at very low frequencies (<10 cells per ml). These levels may provide clinically useful information. However, the laborious procedures required to detect and quantify the presence of circulating tumor cells and the statistics of low numbers introduce a high level of variability in the results. The system of this invention improves upon imaging devices used in a clinical laboratories for rare cell detection in fluid samples such as blood samples (i.e. circulating rare tumor cells of epithelial origin).

Generally, these rare cells are targeted by labeling and separating from blood by magnetic means. The captured cells are fluorescently labeled to permit detection and differentiation from non-target cells and control cells. CellSpotter® is a semi-automated fluorescence microscope that enumerates and differentiates between immuno-magnetically selected cells based upon fluorescence signals from cells in the blood sample.

A blood sample, suspected of containing the targeted rare cells, is preprocessed by enriching the desired rare cells. Enrichment is obtained by linking antibodies, specific for the target cell, to magnetic particles. This immunomagnetic complex is combined with the blood sample in the presence of a magnetic field, providing for the immunomagnetic capture of the target cells. After obtaining an enriched blood fraction containing the target cell, fluorescent reagents are added for subsequent imaging. Enriched cells are placed into a viewing cartridge which then is placed into a magnetic device that directs magnetically labeled cells in the sample to an optically clear planar surface of the chamber for immuno-magnetical alignment and image analysis. The novel sample chamber (U.S. application Ser. Nos. 10/074,900 and 10/303,309) used in the present invention and the Cell Spotter® system are incorporated in the following patents and co-pending applications; U.S. Pat. No. 5,186,827, 5,698,271, 6,120,856, 6,551,843, U.S. application Ser. Nos. 09/702,188, 10/449,355. The magnetic device and chamber are then placed on a fluorescence microscope equipped with a computer controlled filter selector and digitally controlled X-Y-Z stage. Images are acquired by scanning the sample cartridge with 4 different fluorescent filter sets. The acquired images are processed by automated software analysis to compile data containing images of the target cells. Individual frames are viewed and manually selected for target cells. The analysis is complete with a presentation of a gallery of images containing all selected target cells.

When incorporated into a clinical laboratory, the system can be used to examine circulating rare cells associated with clinical disease. For example, multi-center prospective, longitudinal clinical trials can be redially established whereby the number of circulating tumor cells (CTC) are correlated with disease progression in patients having metastatic breast cancer (U.S. Pat. Nos. 6,365,362; 6,645,731; U.S. application Ser. No.10/079,939).

Thus, the principal concepts of the present invention stem from laboratory diagnostic equipment systems assessing the detection and enumeration of cells in biological specimens, together with microscope systems for observing the microstructure of a cell under a desired magnification.

Microscopy technology employing stepper motor driven stages for imaging areas larger than the microscope field of view has limited clinical utility. For example, the achievable speed of image acquisition in image cytometry analysis and the overall lab bench space required for the CellSpotter® System limits it practical clinical use. Currently, image acquisition is accomplished by moving a slide or sample cartridge through the field of view in a boustrophedonic step-by-step motion. A boustrophedonic motion is a motion whereby two consequtive lines along the fastest axis are scanned in opposite directions. One image is taken for each step. When multiple fluorescent images of the same sample are obtained, the filter cube is changed and the boustrophedonic motion is repeated after completion of each pass. This process is repeated until an image is acquired for all positions and all colors, completing a color-by-color scan. Both the movement of the filter cube and the sample is accomplished by stepper motor stages with servo feedback, severly limiting the acquisition speed. Moving a filter cube to the next takes approximately 2 seconds with an additional 0.5 seconds to step between two consecutive positions. Thus, the total acquisition time consists of the total motion time plus the total image acquisition time, making acquisition the predominant time spent on motion with imaging systems like CellSpotter®.

Because the prior art employs stepper motor technology for driving microscope stages which is limited to a maximum driving frequency on the stepper motors, there is a need to develop new devices to improve upon large area image acquisition time. Furthermore, moving the sample (or cartridge) can cause the cells to move with the inertia of the fluid. Any motion of a cell could cause the acquisition software to misinterpret the images and count one cell as two with unpredictable identification.

Another issue with the prior art is that during stage motion the sample is continually being illuminated. Consequently, fluorescent dyes used in cell labeling will undergo bleaching. Phycoeurythin (PE) is a dye comonly used in cell labeling, but very sensitve to bleaching. Reducing the time spent on motion will reduce the extent of sample bleaching.

The equipment encompassed in CellSpotter® technology includes a sample chamber (U.S. application Ser. Nos. 10/074,900, 10/303,309, and U.S. Pat. No. 5,993,665) is placed into a magnetic device (U.S. Pat. No. 5,985,153) that directs magnetically labeled cells in the sample to an optically clear planar surface of the chamber. The magnetic device and chamber are then placed on a fluorescence microscope equipped with a computer controlled filter selector and digitally controlled X-Y-Z stage.

The present invention is an improvement to the CellSpotter® automated diagnostic system to provide rapid sample analysis using multiple fluorescent indicators. The imaging device is further improved by condensing the components into a simple box shape for convienent placement on most clinical laboratory bench tops. This providing a practical configuration in automated laboratories that lack substantial amout of space.

SUMMARY OF THE INVENTION

The present invention provides apparatus and methods to an imaging system for automated operation in a clinical laboratory, improving upon diagnostic imaging devices for rare cell detection used in clinical laboratories. The device of the present invention is a compact and self-contained unit, designed to fit on a laboratory bench top with minimum space in a simple, exterior box-like design. The illumination and collection optics are structured to provide a clinical laboratory technician easy access and use in the analysis of large numbers of patient samples.

Further, stepper motor technology, used in changing the filter cubes and stage movement, has been replaced with nanomotion motors in a closed feedback loop. These movements are critical if an image is to be developed from multiple fluorescent detectors or dyes whereby more than one fliter cube is required. More specifically the motion time for each cube is reduced from 2 to 0.2 seconds for two consecutive filter cubes. The time spent moving between two consecutive positions is reduced from 0.5 to 0.1 seconds. Because the area needed for image acquistion is larger than the system field of view, the acquisition of an entire image requires acquisition of images at several different positions. Nanomotion motors reduce the time period required for these functions and limits the fraction of the total acquistion that is time spent on motion. The majority of time will then be spent on acquition of the image itself, instead of time spent moving the sample and/or cubes. Further with the total acquistion time drastically reduced, the bleaching of the sample, especially with PE, is reduced. The substantial reduction in acquisition time allows for a position-by-position scan of the entire image. With a position-by-position scan, images are acquired for all filter cubes before moving on to the next position in a boustrophedonic motion. Any possible movement of the image during a color-by-color scan is eliminated.

The automated fluorescent optical imaging device of the present invention further provides a prealigned bulb and method for installation/use in the enumeration of fluorescently labeled circulating tumor cells (CTC) that are immuno-magnetically selected and aligned. This invention provides for the standardization of the lamp housing stage through the establishment of a master lamp/stage unit. This master lamp is seated within an adjustment collar as shown in the drawings. The collar has machined gaps which are used to microalign the bulb filament. Thus the collar is used to ensure exact alignment (for X-Y-Z orientation) of the electrodes with respect to any instrument unit. Once aligned, the collar-bulb unit is inserted into a V-block structure for final support. A further improvement to any subsequent shifting in the alignment is the use of a braded wire as a flexible connecting lead. These combined improvements allow for a prealigned bulb to be used in any corresponding imaging unit. This reduces the costs of aligning individual units at their respective locations and provides for efficient installation.

Thus, this automated rare cell imaging device improves upon the speed of sample analysis. The system's compact design in a clinical diagnositic laboratory enables enumeration and identification of target cells for targeting the clinical status of diseases such as metastatic cancer. The pre-aligned buld structure provides rapid, convienent maintenance. Together, these concepts aid in the detection and quantification of target cells in a sample specimen, such as but not limited to, screening and detection in early stage cancer, monitoring for disease remission in response to therapy and selection of more effective dose regimens or alternative therapies in case of relapse.

DETAILED DESCRIPTION OF THE INVENTION

The apparatus of this invention improves upon current CellSpotter® technology to provide a more robust application with less user intervention in a device that is more condusive to a clinical laboratory environment.

Figure 1:
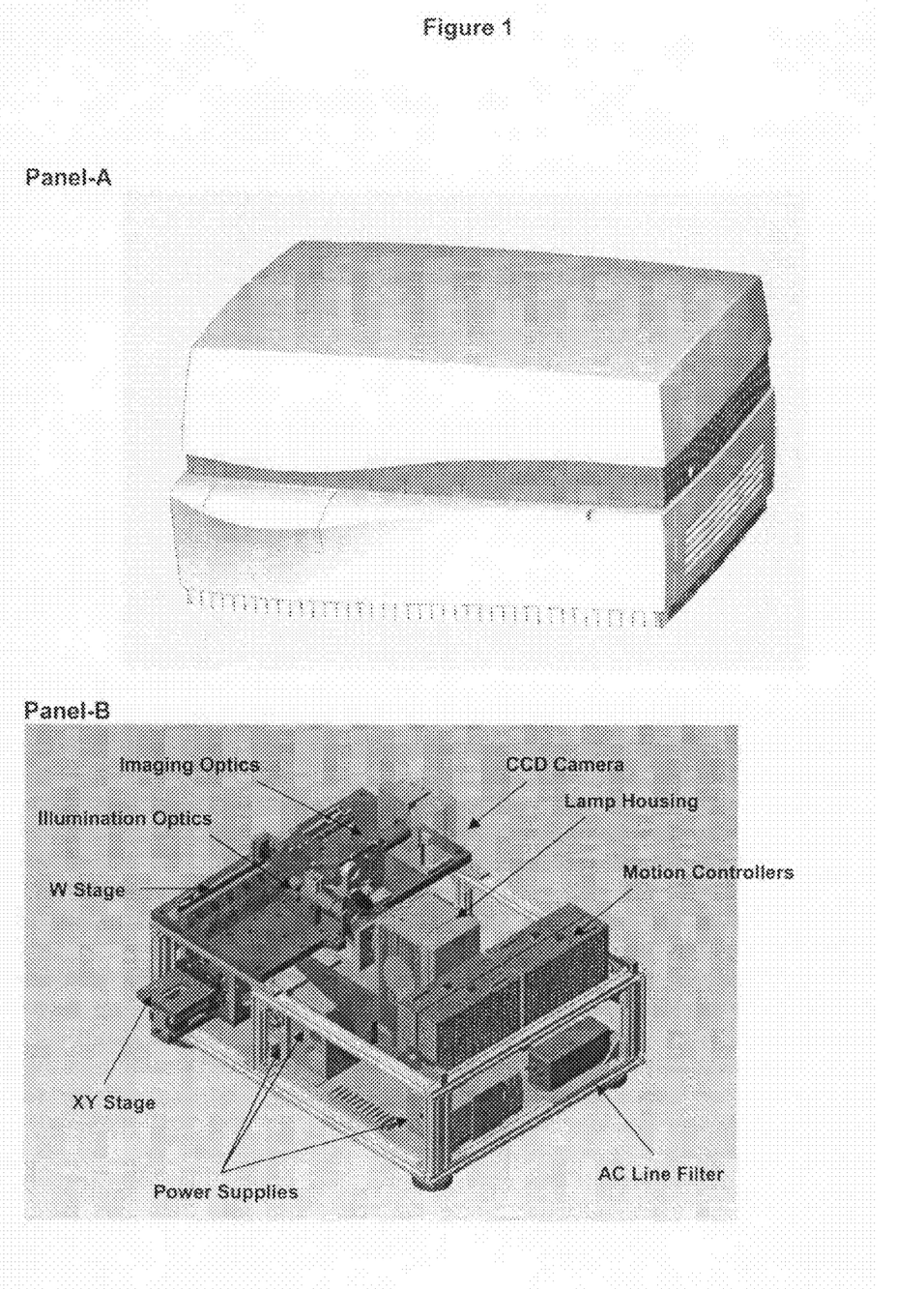
FIG. 1: The overall design of the benchtop profile. (A) Exterior view of box-like unit. (B) Internal view of system components.

First, the overall layout is a non-microscope type design to provide a compact benchtop profile for efficient space management in the laboratory (see FIG. 1). The system is encased in a simple, streamline boxed unit to avoid connecting-cable clutter and to discourage access by laboratory personnel (FIG. 1A). The internal components are designed to provide efficient illumination and collection optics in a confined space (FIG. 1B)

Figure 2:
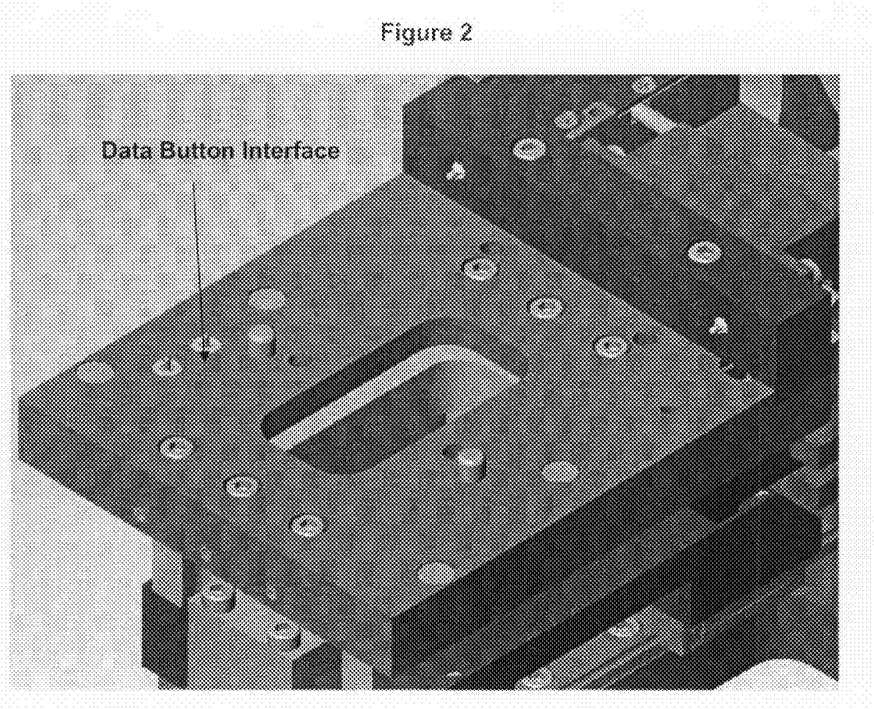
FIG. 2: Modified stage for communication between Mag-NeSt™ and the Imaging System.
Figure 3:
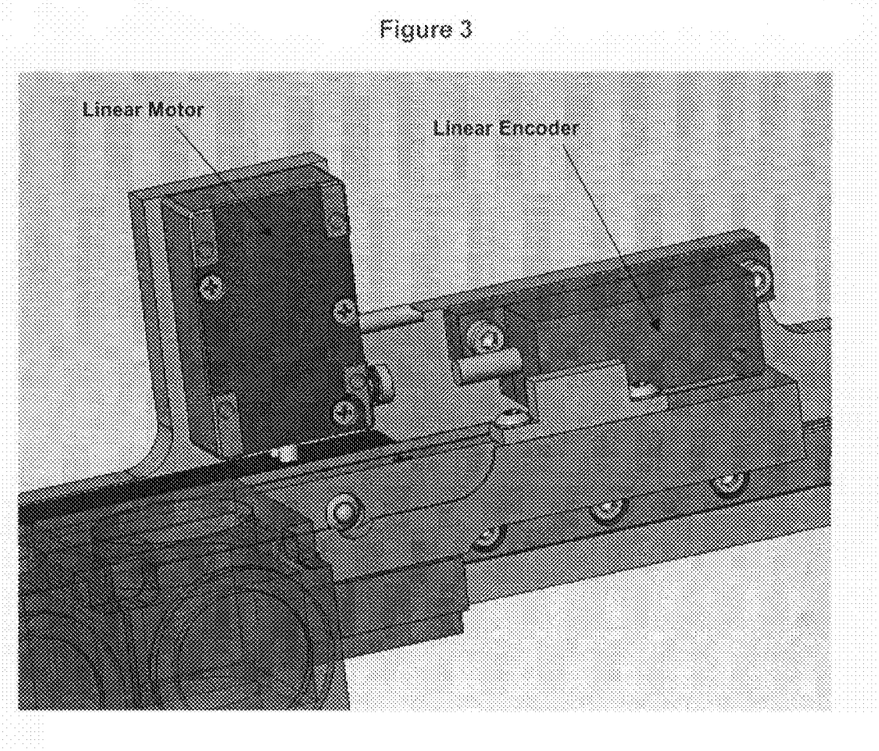
FIG. 3: Diagram showing linear motor and linear encoder relationship to provide positional accuracy.
Figure 4:
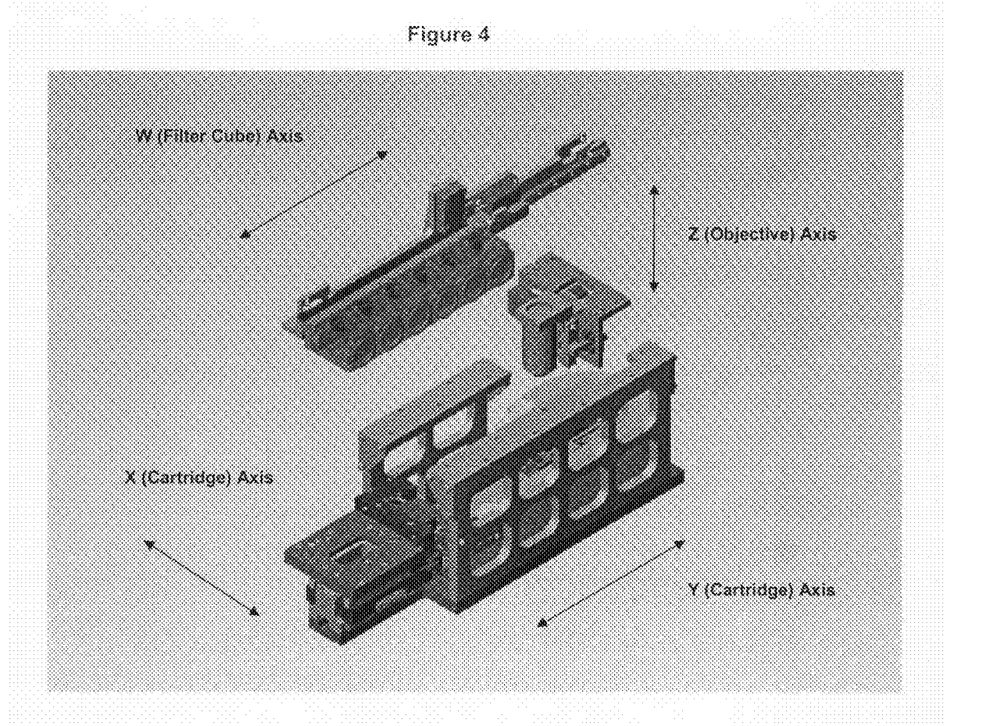
FIG. 4: Diagramatic representation of the axis direction of movement for the filter cube (W), objective (Z), and cartridge (X and Y).

Second, improvements to individual components provide more versatility. The unit can scan an individual sample for multiple analyses. Further, the unit is expandable to include multiple analyte specific reagents (ASR) and the associated software algorithms. MagNest™, the magnetic device, communicates to the stage through a data button interface (see FIG. 2). The stage is improved in both accuracy (see FIG. 3) and precision. The platform motion functions through a motion controller (Galil), piezoelectric motor (Nanomotion), and position encoders (Renishaw). This provides 0.2 micron resolution on the X, Y, Z plane and with the filters (W), as shown in FIG. 4. The optical components include an Oriel Lamp Assembly with an integrated Nikon lens which is operator adjustable. The lens system has very few components to reduce the amount of light lost in surface reflections and the illumination approach is more efficient than the commonly used Kohler illumination. The 10×objective and 100 W mercury arc lamp as a light source are similar to the prior design.

Figure 5:
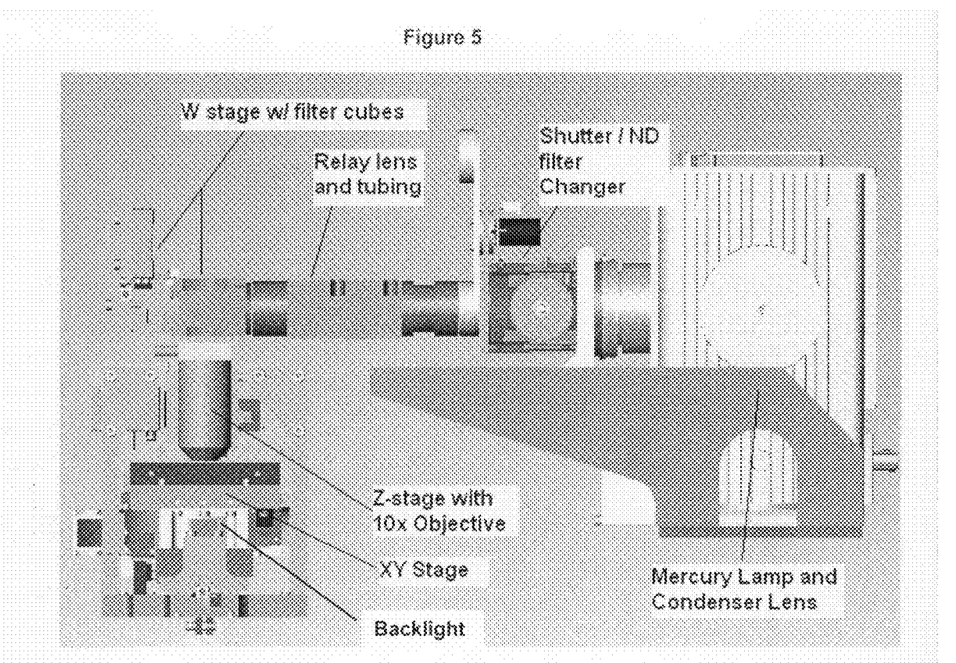
FIG. 5: Diagram showing illumination path in relation to instrument components.
Figure 6:
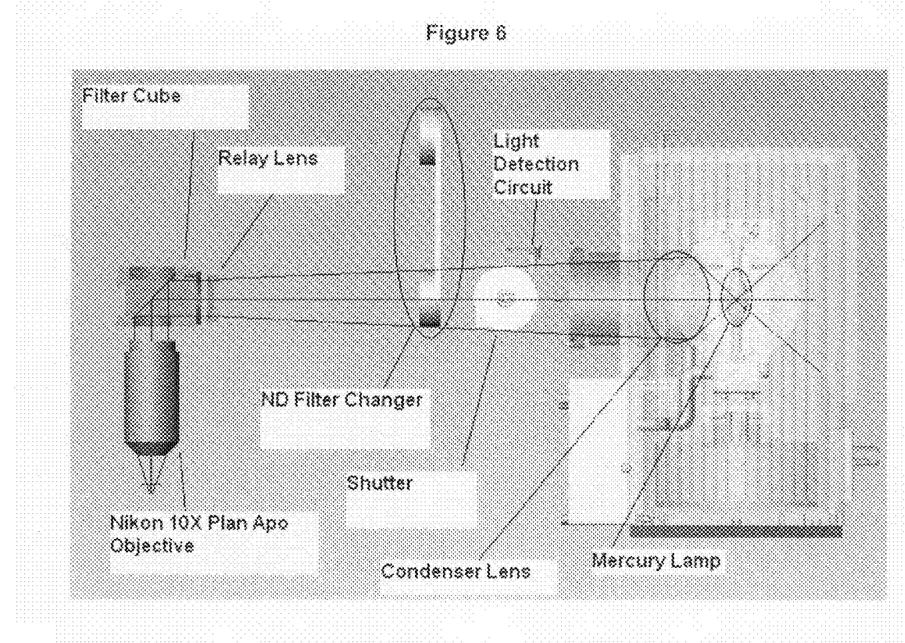
FIG. 6: Diagram of illumination path showing light path.

Critical to the compact design is the unique illumination path, together with the stage placement allowed the prior microscope structure to fit into the new shape (FIG. 5). The resulting illumination path allows easy access to the associated lens, filters, and light source (FIG. 6). The illumination system has a fluorescence excitation range capable of wavelengths from 350 to 1000 nanometers. The intensity and uniformity are approximately equivalent to CellSpotter®, even though the lamp housing does not have a rear reflector.

The mercury lamp is equivalent to CellSpotter® with the number of adjustment knobs reduced to 3 (not the previous 6). This facilitates user replacement of the lamp.

Figure 7:
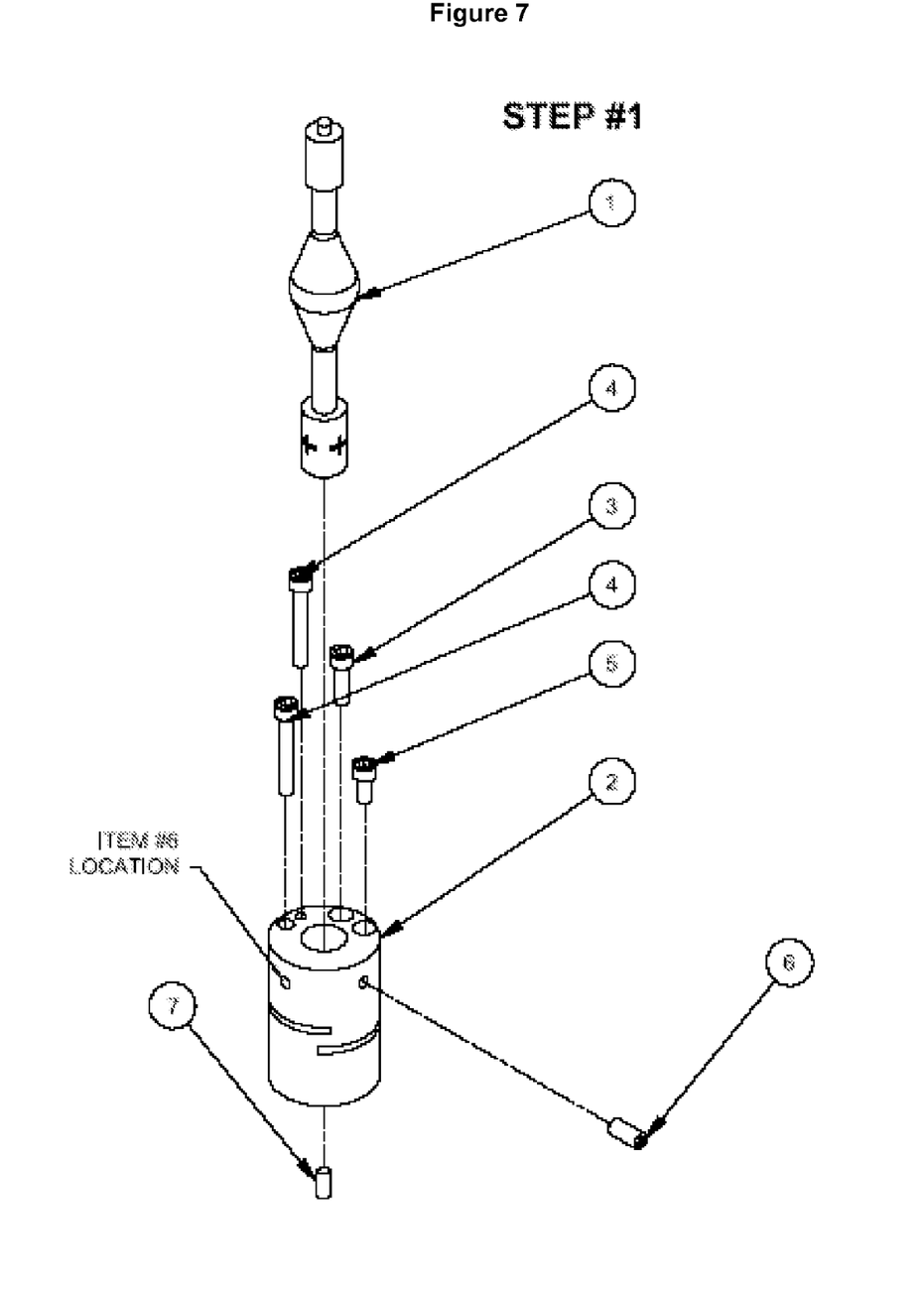
FIG. 7: Diagram of the pre-aligned structure showing the lamp (1) with support collar (2). Adjustment screws (3), (4), and (5) are on the top portion of the collar while adjustment screw (6) is located on the lateral surface and adjustment screw (7) is on the bottom.
Figure 8:
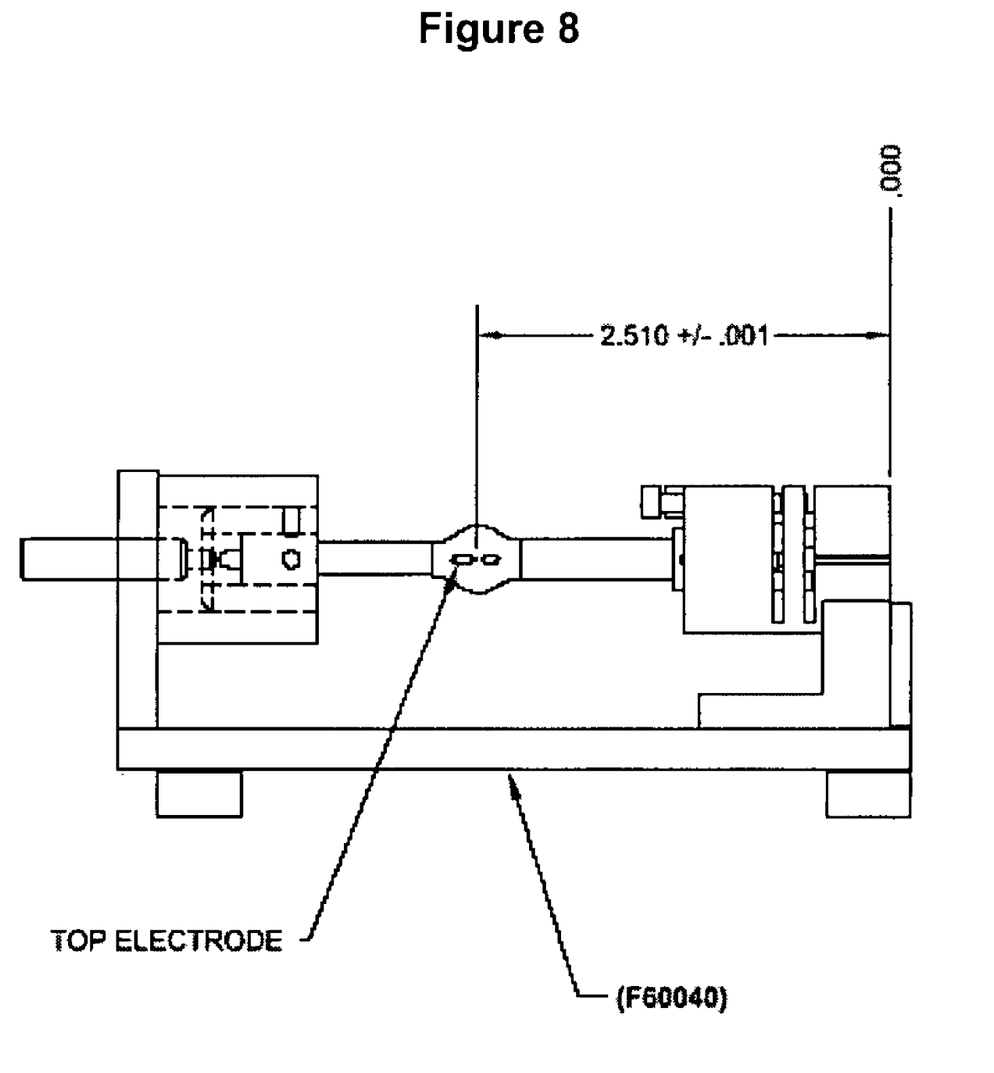
FIG. 8: Schematic representation of the alignment fixture-F60040 with lamp with electrode in position.
Figure 9:
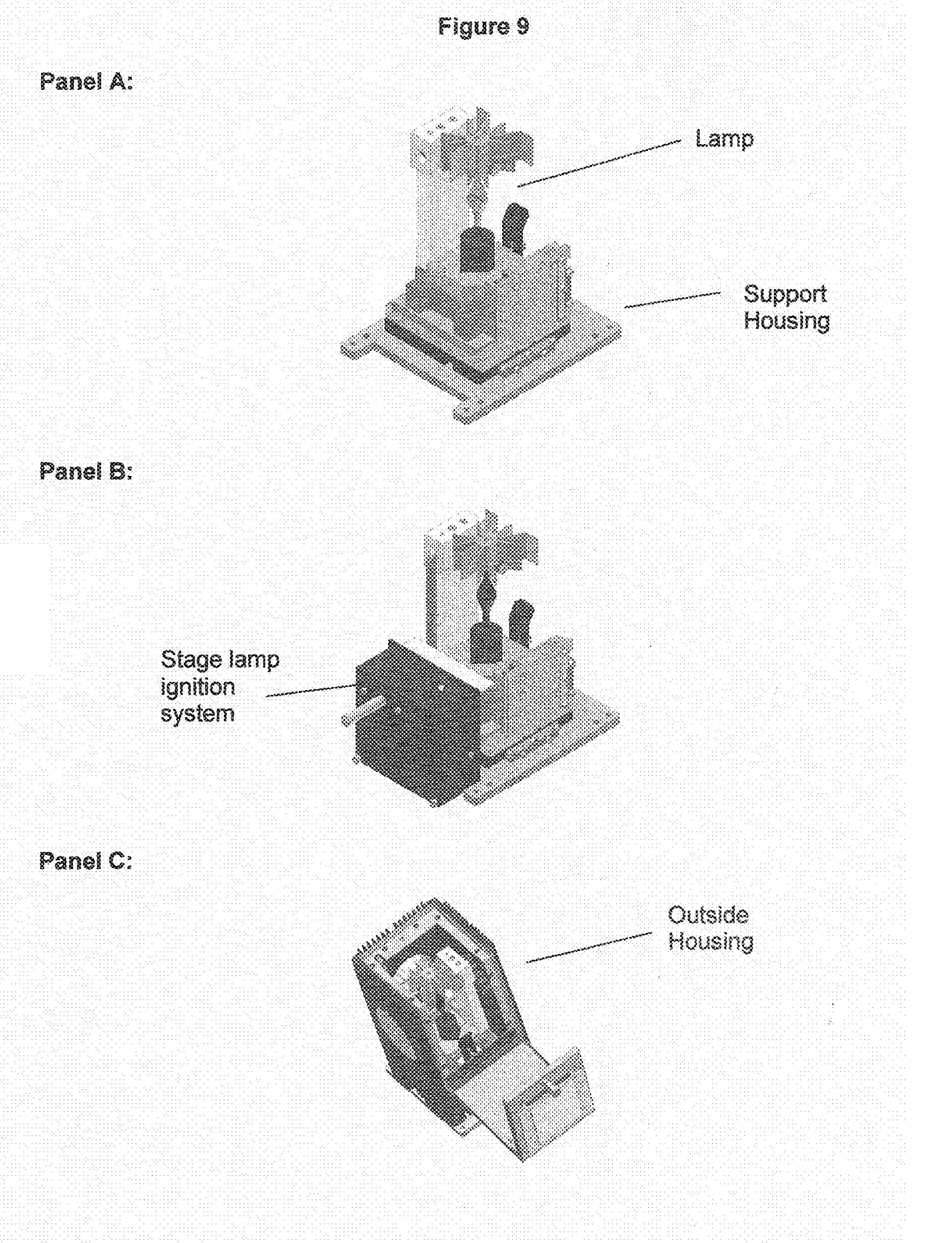
FIG. 9: Diagram of the complete support apparatus for the lamp. Panel A shows the support apparatus with the lamp. Panel B shows the apparatus with the stage lamp ignition system in place. Panel C shows the apparatus with the outside housing.

The present application also incorporates the optional use of a pre-aligned lamp system. FIG. 7 depicts the collar (2) in relation to the lamp (1) with adjustment screws (3), (4), (5), (6), and (7) optimally located on the collar surface. As shown in FIG. 8, the alignment fixture F60040 is used on an optical comparitor (i.e. 50×lens) to zero out at dimension 0.000 and adjust top electrode positon to 2.510±0.001 using adjustment screw (7). Adjustment screws, 3-4-5, are used to align top electrode (1) with horizontal center line on optical comparator with horizontal tolerance to be no wider than bottom electrode thickness. These steps are continued until the top electrode is aligned to the horizontal center line on the optical comparitor. The lamp is a 100 W mercury bulb. FIG. 9 shows the complete support apparatus for the lamp. Panel A is with the lamp and support alone. Panel B is with the associated stage lamp ignition system and panel C is with the outside housing in place.

Figure 10:
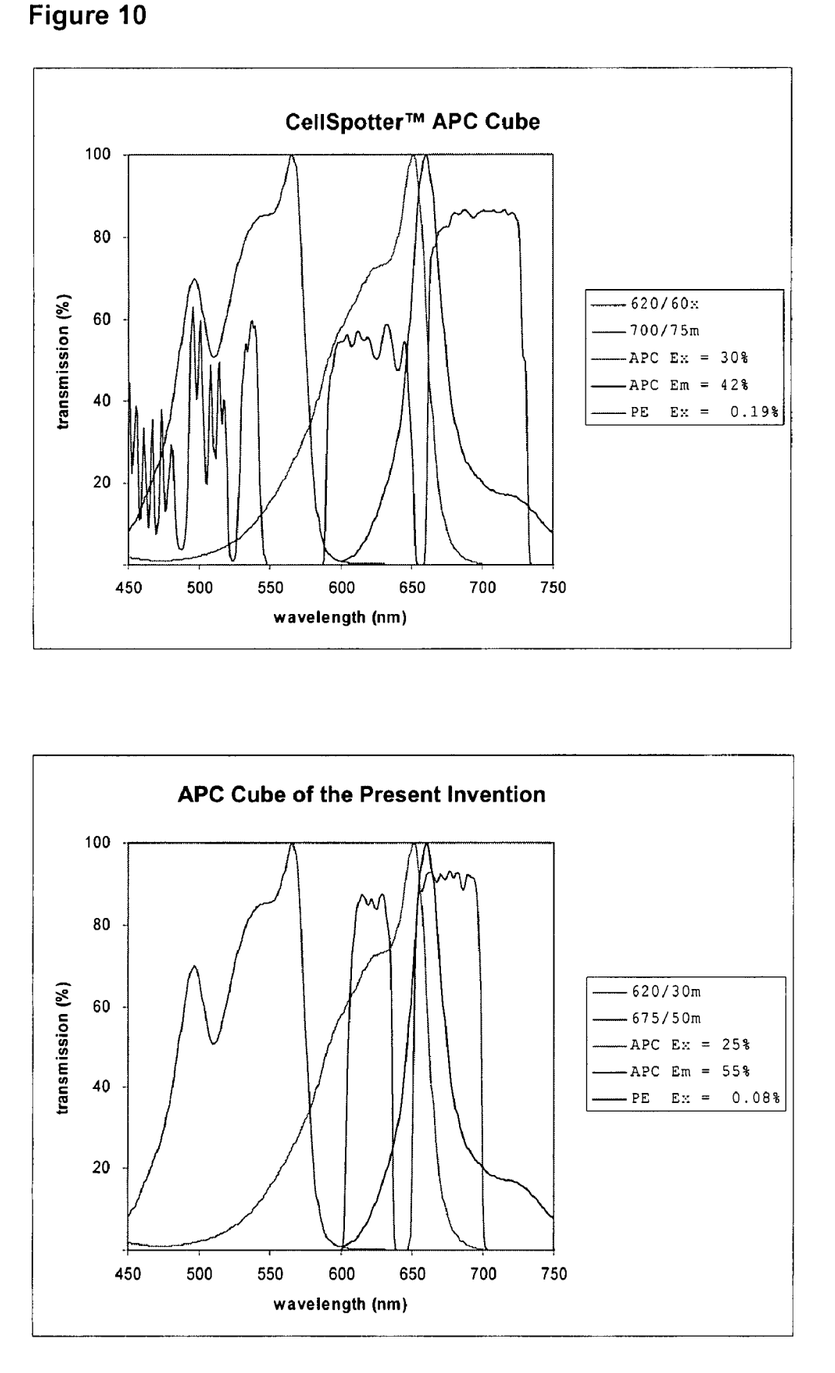
FIG. 10: Comparision of CellSpotter APC Cube with the APC Cube of the Present Invention.

The filter cubes are similar to CellSpotter®, but the filter cube number is expanded from four (4) to six (6). The DIOC/PE cube is unchanged. APC cube is now modified to reduce the number of dual positives while maintaining the sensitivity. The DAPI cube is improved to reduce autofluorescence and leaking of the cube. The APC cube is also improved to reduce PE bleed-over (approximately 50%) with fewer bright CTC showing up in the APC channel, while maintaining APC sensitivity. APC detection efficiency is identical to CellSpotter®. Additional ASR tags that can be supported with the present invention include IRQdot with 1 ASR (Ex=350 nm and Em=800 nm), lanthanides with 2 ASR's (ex=350 nm, Em=615 nm (Eu) and 550 nm (Tb)), and UPT with 2 ASR's (Ex=980 nm, Em approximately 490 and 580 nm). Further improvements include a bar-coded latex and spectral compensation. These factors improve the APC cube with reduced PE bleed (50%) with fewer bright CTC in the APC channel (FIG. 10). Further the APC efficiency is identical with no loss in the percent white blood cells detected.

There is a further improvement in the present device in the backlight design. The backlight is used for finding edges of the cartridge, initial alignment of the instrument and optional brightfield imaging. An LED is used as a light source. Uniformity is good (CV of 2.5%).

The detection system is improved over CellSpotter® with better resolution, sensitivity, dark noise, dynamic range and field flatness. Wavelenghts of 400 to 800 nm can be detected, with the option to expand to 400-1100 nm at the cost of a small fraction in the MTF (modulation transfer function).

Figure 11:
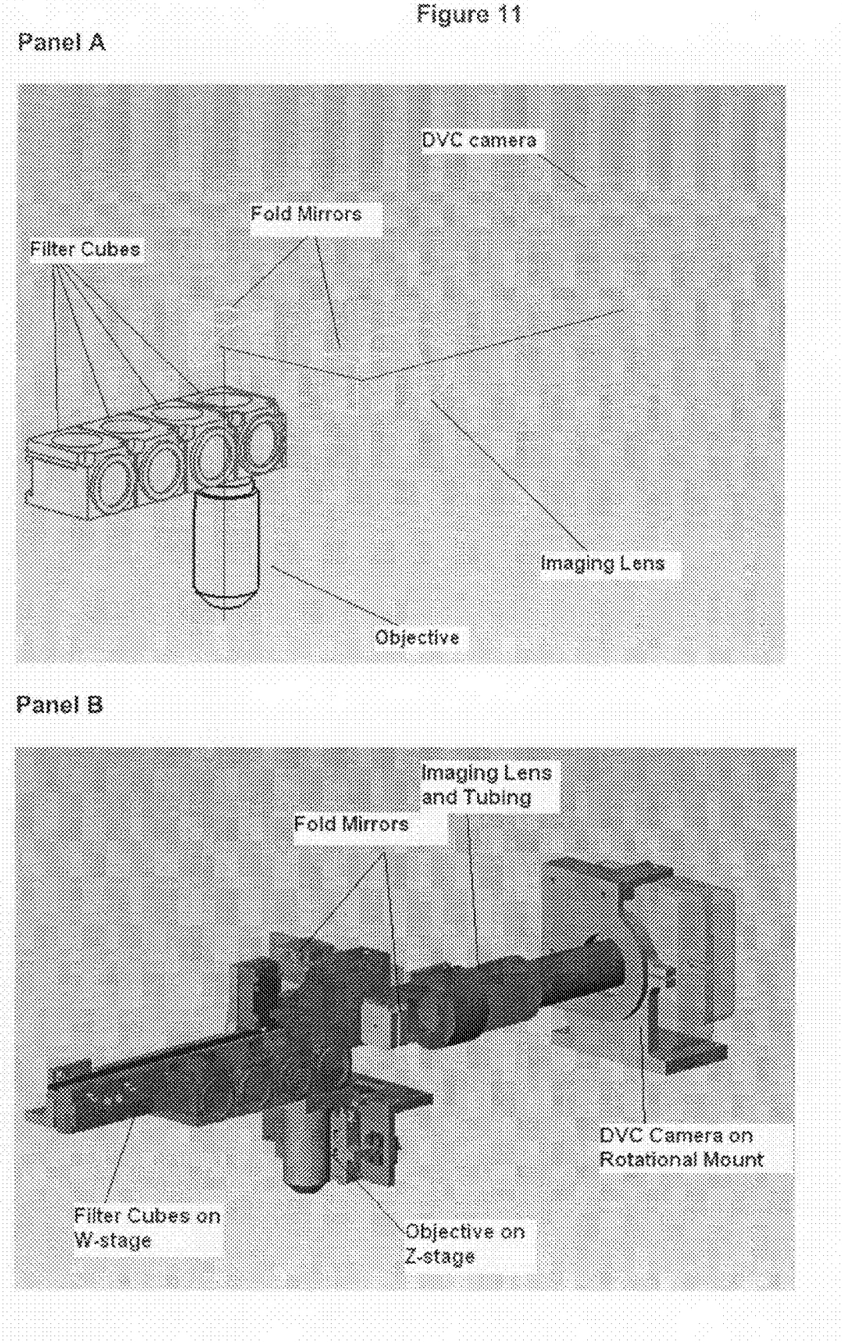
FIG. 11: Diagram of imaging path with direction of light in relation to camera, lens, mirrors, cubes and objective (Panel A). Imaging path shown with apparatus in position (Panel B).

The imaging path is shown in FIG. 11. Panel A depicts the light path while Panel B shows the apparatus.

The chip width is 3% smaller which results in a high number of scans with 175 frames (i.e. 1 extra row) per filter. The sample chamber width is reduced by 5% which restores the scan to 4 rows (140 frames) with 3 sigma certainty and reduces the volume of the chamber by 15 microliters.

The present device has a 2 stage TE cooled CCD chip. The cooling reduces dark current. The present device also considers one stage TE cooling which is sufficient to meet dark current specification (with internal system temperature less than 40° C.), offering a cheaper detector option.

The present invention also considers the use of a 40×objective lens alone or in combination with the current 10x objective lens used in image acquisition. The total time for acquisition of the image constitutes 5 components. These include time spent to set up the system/moving to eject position, to move the sample in the x-y direction, to move the filter cube, to acquire an image (integration time), and to transfer the image.

The total acquisition time for a color-by-color approach, whereby first the entire cartridge is imaged with the first cube, followed by the next cube. This is compared with the position-by position approach, whereby acquired images for all colors are obtained for each position before moving on to the next position. A diagramatic representation of the acquistion times is shown in the table below (Table 1). DAPI, PE, FITC and APC using CellSpotter® are shown by exempliary illustration, and are not to limit the embodiment of the present invention.

TABLE I

One color all positions before moving to the next color

| | Start | DAPI Acquisition | | PE Acquisition | | FITC Acquisition | | APC Acquisition | | Return |
|---|---|---|---|---|---|---|---|---|---|---|
| | | pos 1 | pos 140 | pos 1 | pos 140 | pos 1 | pos 140 | pos 1 | pos 140 | |
| Initial/final move | | | | | | | | | | |
| Move xy | | | | | | | | | | |
| Move Filter | | | | | | | | | | |
| Acquire Image | | | | | | | | | | |
| Transfer Image | | | | | | | | | | |

TABLE I-continued

All colors one position before moving to the next position

| | Start | Position 1 | | | | Position 140 | | | | Return |
|---|---|---|---|---|---|---|---|---|---|---|
| | | DAPI | PE | FITC | APC | DAPI | PE | FITC | APC | |
| Initial/final move | | | | | | | | | | |
| Move xy | | | | | | | | | | |
| Move Filter | | | | | | | | | | |
| Acquire Image | | | | | | | | | | |
| Transfer Image | | | | | | | | | | |

The time spent acquiring individual images is the same in both methods, but different for different dyes, 0.11 sec for DAPI, 0.22 sec for PE, 0.11 sec for FITC, and 0.66 sec for APC. Comparision of the color-by-color method with the position-by-positon method shows that the main diffence is that the total time spent is affected by the time to move the sample in the x-y direction.

The total color-by color time is modeled by the following:

$$T_{color\text{-}by\text{-}color} = T_{init} + 140 \times T_{acquisition} + 560 \times (T_{move\,xy} // T_{transfer}) + 4 \times T_{move\,filter} + T_{final} \quad (1)$$

For the position-by-position the model is given by the following:

$$T_{position\text{-}by\text{-}position} = T_{init} + 140 \times T_{acquisition} + 140 \times (T_{move\,xy} // T_{transfer} // T_{move\,filter\,4\text{-}1}) + 420 \times (T_{move\,filter\,1\text{-}2/2\text{-}3/3\text{-}4} // T_{transfer}) + T_{final} \quad (2)$$

where (A//B) means A if (A>B) and B if (A≦B).

Assuming the following values for CellSpotter® system, $T_{init+Tfinal}=60$ seconds, $T_{acquisition}=1.1$ seconds, $T_{transfer}=0.11$ seconds, $T_{move\,xy}=0.5$ seconds, $T_{move\,filter}=2$ seconds, $T_{move\,filter\,4-1}=6$ seconds, the resultant total acquisition time is 500 seconds (8 minutes 20 sec) for the color-by-color approach and 1900 seconds (31 minutes 40 sec) for the position-by-position approach.

In the present invention, these times are the following; $T_{acquisition}=0.6$ seconds, $T_{transfer}=0.11$ seconds, $T_{move\,xy}=0.1$ seconds, $T_{move\,filter}=0.2$ seconds, $T_{move\,filter\,4-1}32\,0.5$ seconds.

The higher QE of the ICX285 chip reduces $T_{acquisition}$ time while the reduction in time for $T_{move\,xy}$ and $T_{move\,filter}$ are due to the nanomotion stages and filter changer, respectively. The reduced times result in total times of 200 seconds (3 minutes 20 seconds) and 300 seconds (5 minutes) for color-by-color and position-by-position approach, respectively. Total acquisition times for both approaches are substantially reduced. So while the color-by-color is still faster, the difference is small enough to make the position-by-position more practical. In fact, the reduced acquisition time allows imaging with PE without significant interference from bleaching.

A further advantage of the position-by-position approach is that the cells stay aligned.

Finally, the present device is designed to provide easily replaceable units in the field to allow rapid, low cost service calls. These units include power supplies, X-Y stage assembly, Z-stage assembly, filter (W) stage assembly, servo amplifiers (4), CCD camera, imaging and illumination optics assembly, objective, filter cubes, lamp and housing, computer and peripherals, shutter/ND filter assembly, air filters, main circuit board and cables.

Safety provisions include an enclosure interlock closing system shutter. The lamp housing interlock disables the lamp supply. UV filter safety glasses are supplied with the instrument. The instrument can operate in the US, Europe and Japan without switching any components.

It is to be understood and appreciated that these improvements are only illustrative of the many additional potential applications of the apparatus and method that may be envisioned by one of ordinary skill in the art, and thus are not in any way intended to be limiting of the scope of the invention.

What is claimed is:

1. A clinical laboratory automated imaging system for detecting rare cells from a biological sample comprising:
    a. an illumination system having an optimum illumination path whereby said path allows for compact design;
    b. an X-Y-Z stage assembly motioned through piezoelectric motors and having a platform to position a magnetic device and sample cartridge for imaging;
    c. a fluorescent detection system having at least one APC filter cube motioned through piezoelectric motors wherein said APC cube reduces PE bleed-over by approximately 50% while maintaining APC sensitivity; and
    d. a computer with related peripherals wherein elements a, b, c and d of the system form a compact and self-contained structure in an optimized size for use on a laboratory bench top.

2. The illumination system of claim 1 whereby said illumination system consists of a CCD camera, illumination optics assembly, objective, filter cubes, lamp with housing, and shutter/ND filter assembly.

3. The illumination system of claim 2 whereby said lamp is pre-aligned.

4. The illumination system of claim 1 whereby said illumination path allows easy access to associated lenses filters and light source.

5. The illumination system of claim 1 with the capability to produce fluorescence excitation wavelengths between 350 to 1000 nanometers.

6. The X-Y-Z stage assembly of claim 1 wherein motion of said stage is through said piezoelectric motor capable of providing 0.2 micron resolution.

7. The detection system of claim 1 wherein said detection system contains a backlight structure for alignment of said sample cartridge.

8. The detection system of claim 1 wherein the chip width is small enough to scan 175 frames per filter.

9. A method for acquiring multiple images from a sample cartridge by a color-by-color approach comprising:
   a. setting system to an image position;
   b. moving cartridge sample in the x-y direction corresponding to said position whereby said moving is with a piezoelectric motor;
   c. positioning a filter cube;
   d. acquiring said image;
   e. transferring said image; and
   f. repeating elements c through e for an x-y position whereby said repeating is for each filter cube wherein at least one filter cube is APC having reduced PE blood-over by approximately 50% while maintaining APC sensitivity.

10. A method for acquiring multiple images from a sample cartridge by a position-by-position approach comprising;
   a. positioning a first filter cube;
   b. setting system to an image position;
   c. moving cartridge sample in the x-y direction corresponding to said position;
   d. acquiring said image;
   e. transferring said image;
   f. repeating elements b through e for each x-y position; and
   g. positioning another filter cube to complete elements b through f whereby said elements are repeated for each cube and said positioning with a piezoelectric motor, wherein at least one filter cube is APC having reduced PE blood-over by approximately 50% while maintaining APC sensitivity.

* * * * *